United States Patent
Euvrard et al.

(10) Patent No.: US 7,771,198 B2
(45) Date of Patent: Aug. 10, 2010

(54) DENTAL POWER INSTRUMENTS, SUCH AS ENDODONTIC INSTRUMENTS, AND CONTRA-ANGLE HANDPIECE

(75) Inventors: Hubert Euvrard, Besançon (FR); Jean-Philippe Mallet, Paris (FR); Etienne Deveaux, La Madeleine (FR)

(73) Assignee: Micro Mega International Manufactures, Besançon (FR)

( * ) Notice: Subject to any disclaimer, the term of this patent is extended or adjusted under 35 U.S.C. 154(b) by 435 days.

(21) Appl. No.: 10/542,451

(22) PCT Filed: Oct. 20, 2003

(86) PCT No.: PCT/FR03/03091

§ 371 (c)(1), (2), (4) Date: Jul. 15, 2005

(87) PCT Pub. No.: WO2004/071325

PCT Pub. Date: Aug. 26, 2004

(65) Prior Publication Data

US 2006/0121414 A1    Jun. 8, 2006

(30) Foreign Application Priority Data

Jan. 15, 2003    (FR)    .................................. 03 00474

(51) Int. Cl.
*A61C 1/08*    (2006.01)
*A61C 3/02*    (2006.01)
*A61C 1/12*    (2006.01)

(52) U.S. Cl. ........................ 433/126; 433/133; 433/165

(58) Field of Classification Search ......... 433/124–128, 433/13, 165, 209
See application file for complete search history.

(56) References Cited

U.S. PATENT DOCUMENTS

| | | | |
|---|---|---|---|
| 1,688,136 A * | 10/1928 | Chayes et al. ................. 279/76 |
| 1,875,559 A | 9/1932 | Brumm | |
| 2,005,849 A | 7/1935 | Skinner | |
| 2,231,969 A | 2/1941 | Tifft | |
| 2,344,605 A | 3/1944 | Droegkamp | |
| 2,568,315 A | 9/1951 | Björklund | |
| 2,813,337 A | 11/1957 | Uhler | |
| 3,070,381 A | 12/1962 | Saffir | |
| 3,098,299 A | 7/1963 | Page | |
| 3,163,934 A | 1/1965 | Wiseman | |

(Continued)

FOREIGN PATENT DOCUMENTS

DE    855305    11/1952

(Continued)

*Primary Examiner*—Cris L Rodriguez
*Assistant Examiner*—Yogesh Patel
(74) *Attorney, Agent, or Firm*—Gary M. Cohen

(57) ABSTRACT

A dental power instrument, in particular, an endodontic instrument, has an operative part (2) at one end and a handle (3) at the opposite end. The handle (3) of the dental instrument is provided with a rotary drive (4) which, when mounted in the head (5) of a handpiece, can directly engage with a rotary drive (4') upstream of the head. The rotary drive (4) can be inserted and withdrawn independently of the rotary drive (4') associated with the head of the handpiece, and rotates in the same direction as the rotary drive (4') associated with the handpiece. Also provided is a handpiece head (5) and a dispenser (30) for such dental power instruments.

22 Claims, 3 Drawing Sheets

U.S. PATENT DOCUMENTS

| | | | | |
|---|---|---|---|---|
| 3,368,279 | A | 2/1968 | Weissman | |
| 3,381,378 | A | 5/1968 | Lawrence et al. | |
| 3,472,045 | A | 10/1969 | Nelsen et al. | |
| 3,578,745 | A | 5/1971 | Blanc et al. | |
| 3,751,176 | A | 8/1973 | Von Hollen | |
| 3,955,284 | A | 5/1976 | Balson | |
| 3,961,422 | A * | 6/1976 | Riitano et al. | 433/75 |
| 4,014,099 | A | 3/1977 | Bailey | |
| 4,021,920 | A | 5/1977 | Kirschner et al. | |
| 4,285,671 | A | 8/1981 | Lustig et al. | |
| 4,406,470 | A | 9/1983 | Kataoka et al. | |
| 4,449,932 | A * | 5/1984 | Lustig | 433/126 |
| 4,451,237 | A | 5/1984 | Filhol | |
| 4,478,578 | A | 10/1984 | Leonard | |
| 4,486,175 | A | 12/1984 | Fisher et al. | |
| 4,564,354 | A | 1/1986 | Rosenstatter | |
| 4,711,630 | A | 12/1987 | Dürr | |
| 4,874,314 | A | 10/1989 | Fleer et al. | |
| 5,007,832 | A | 4/1991 | Meller et al. | |
| 5,020,994 | A | 6/1991 | Huang | |
| 5,028,233 | A | 7/1991 | Witherby | |
| 5,040,978 | A | 8/1991 | Falcon et al. | |
| 5,120,220 | A | 6/1992 | Butler | |
| 5,156,547 | A | 10/1992 | Bailey | |
| 5,160,263 | A | 11/1992 | Meller et al. | |
| 5,209,658 | A | 5/1993 | Brahler | |
| 5,252,067 | A | 10/1993 | Kakimoto | |
| 5,308,242 | A | 5/1994 | McLaughlin et al. | |
| 5,647,745 | A * | 7/1997 | Badoz | 433/126 |
| 5,730,595 | A | 3/1998 | Bailey | |
| 5,941,705 | A * | 8/1999 | Makris et al. | 433/141 |
| 6,065,966 | A | 5/2000 | Krause et al. | |
| 6,155,827 | A * | 12/2000 | Euvrard | 433/133 |

FOREIGN PATENT DOCUMENTS

| | | |
|---|---|---|
| DE | 1018190 | 10/1957 |
| FR | 2618357 | 1/1989 |
| FR | 2692473 | 12/1993 |
| GB | 587856 | 5/1947 |

* cited by examiner

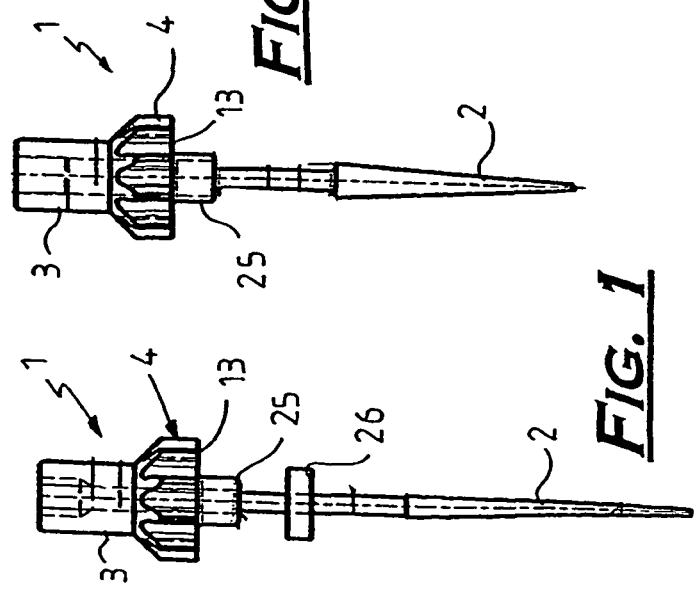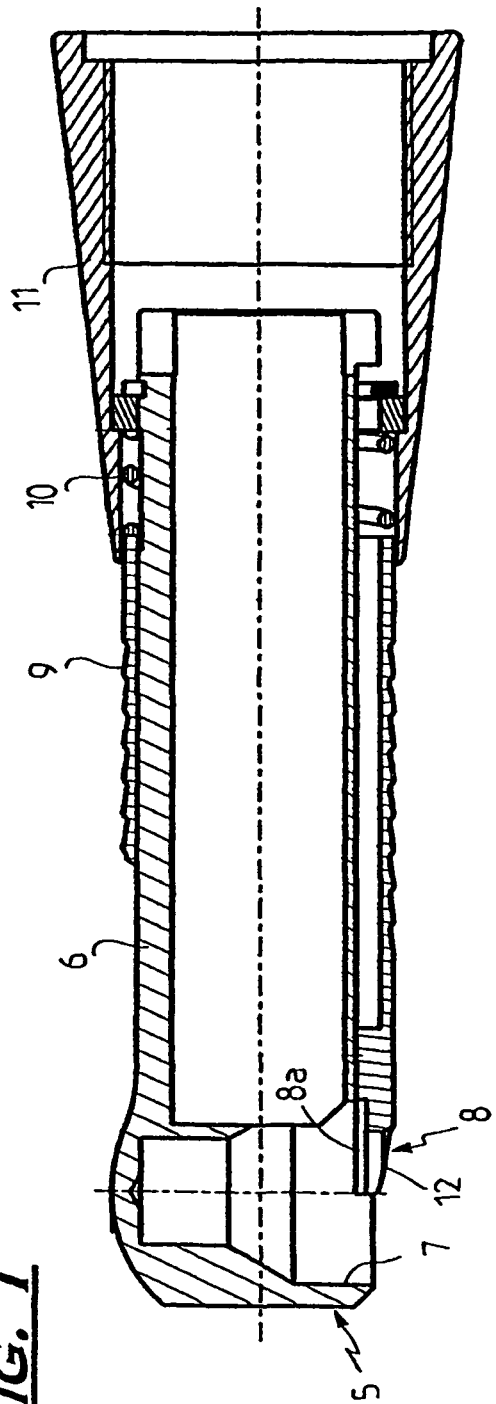

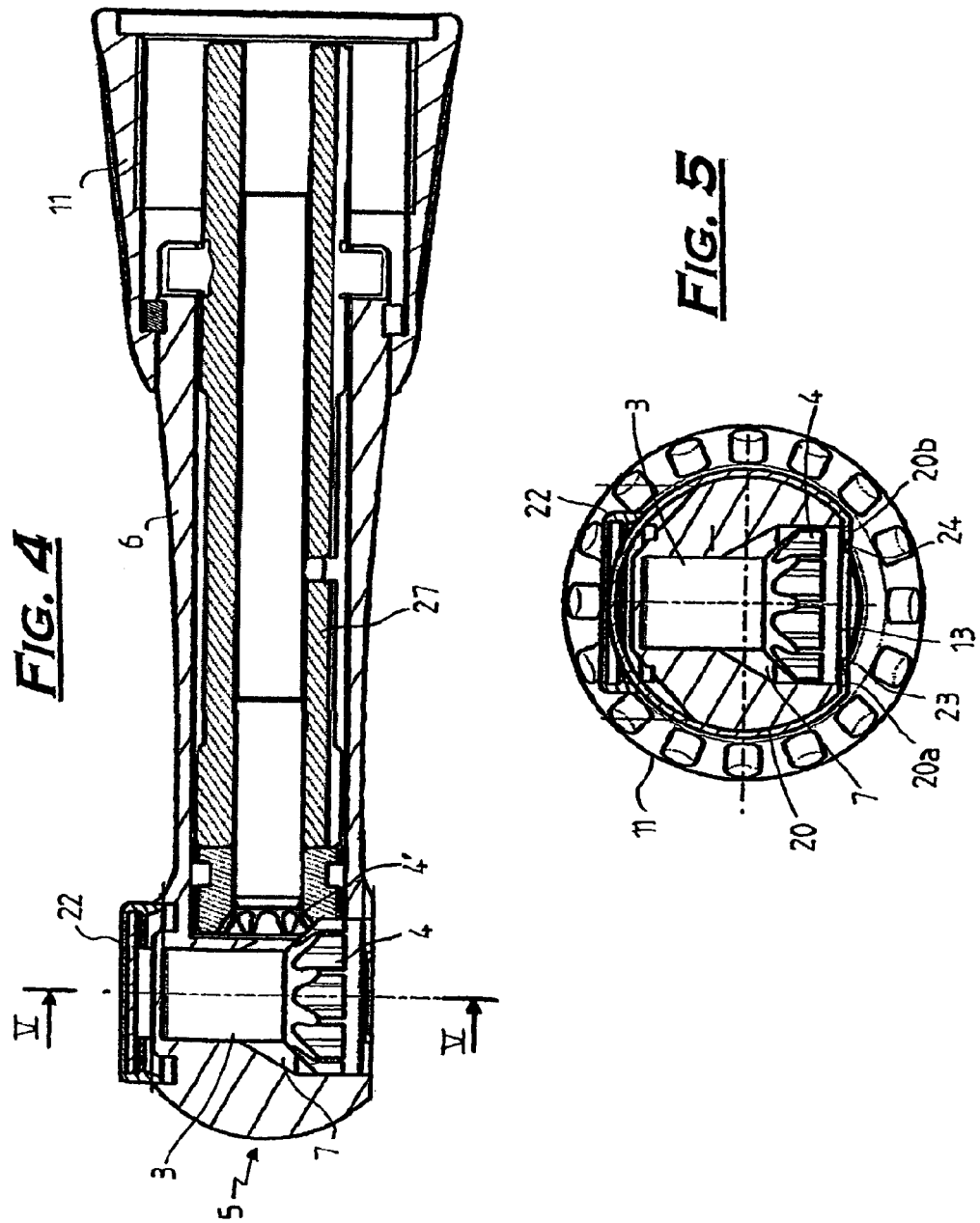

DENTAL POWER INSTRUMENTS, SUCH AS ENDODONTIC INSTRUMENTS, AND CONTRA-ANGLE HANDPIECE

BACKGROUND OF THE INVENTION

The present invention relates to improved dental power instruments such as endodontic instruments, and a contra-angle drive apparatus or handpiece designed to removably accommodate such instruments.

Dental power instruments are usually provided with a handle, located at an end opposite to the active part of the instrument, for engaging a revolving guiding and gripping device situated in the head of the handpiece. The handle also includes a flat for engaging the profile of a rotary drive housed in the head of the contra-angle, to connect the handle to the rotary drive.

The guiding and gripping device usually includes a retainer, such as a pushbutton or a guillotine, which is controllable by the user. The handle of the instrument is further axially engaged in the head of the contra-angle by a device on the rotating part of the contra-angle which fits into a groove in the handle of the instrument.

Such a system for fixing the instrument handle in the head of the contra-angle requires a great many mechanical parts, which leads to a high cost of manufacture.

Another disadvantage of such a system is that in order to mount the dental instrument in, or to remove the dental instrument from the head of the contra-angle, the practitioner must hold the instrument by its active part. This leads to a risk of contaminating the active part of the instrument, and even a risk of injury to the practitioner, for example, by prick injury.

The object of the present invention is to provide an improvement to such dental instruments that solves some or all of the aforementioned problems by providing an inexpensive way of fitting the instrument to the head of a handpiece shaped to receive such an instrument, while also reducing the risk of contamination of the active part of the instrument and of injury to the practitioner.

SUMMARY OF THE INVENTION

To this end, the present invention relates to a dental power instrument, and in particular to an endodontic instrument, which includes an active part at one end and a handle at the end opposite to the active part. The handle of the dental instrument is provided with a rotary drive which is capable of meshing directly with a rotary drive situated upstream of the head of the handpiece when mounted in the head of the handpiece. The rotary drive of the dental instrument is retractable independently of the rotary drive of the head of the handpiece, and has the same direction of rotation as the rotary drive of the head of the handpiece.

Advantageously, the rotary drive associated with the handle of the dental instrument is a pinion. The dental instrument of the present invention also advantageously includes a shoulder adjacent to the rotary drive, on the side of the rotary drive nearest to the active part of the instrument. The shoulder permits the handle of the instrument to be raised when placed on a dispenser, in this way facilitating engagement of the instrument in the head of the handpiece.

The present invention also relates to the head of a handpiece for receiving the previously described dental instrument. To this end, the head is provided with a bore, which forms a housing for the handle of the dental instrument, and with a retractable retainer for axial engagement of the handle of the dental instrument which is capable of being operated by the practitioner.

The retractable retainer advantageously includes a part which projects across the opening of the housing. This projecting part is further connected to a ring which can be moved against the action of a restoring spring and which is mounted concentrically on the outer periphery of the body of the head. The projecting part has a horseshoe profile, for a complete fit with the shape of the shoulder formed on the dental instrument, and further includes a retraction slope on its outer face which is designed to engage with a combined profile on the handle of the dental instrument, so that when the handle is inserted into the head of the handpiece, the combined profile of the handle causes the retainer to retract.

In an alternative embodiment, the retainer is a spring split ring arranged on the head of the handpiece so that, in a rest position, the ends of the split ring project into the mouth of the opening of the housing for the handle of the instrument. The split ring is retractable, responsive to a pushbutton located on top of the head, and each of the ends of the split ring is provided with a retraction slope for engaging the end of the handle of the instrument to push back the split ring and allow access to the housing of the head. Each of the ends of the split ring also advantageously has a horseshoe profile, for a complete fit with the shape of the shoulder formed on the dental instrument.

The present invention also relates to a dispenser for the previously described dental instruments which includes a plurality of instrument-receiving housings, and a cover situated above the instruments contained in the housings of the dispenser. The cover has an opening for allowing the head of the contra-angle to access and engage the handle of an instrument, and can be turned manually to position the opening over an instrument. The cover also has an indexing apparatus for positioning the opening of the cover over each of the instrument-receiving housings.

These and other features of the present invention are further discussed in the description of illustrative embodiments which is provided hereafter, with reference to the following drawings.

BRIEF DESCRIPTION OF THE DRAWINGS

FIGS. 1 and 2 are side views of two dental power instruments produced in accordance with the present invention.

FIG. 3 is a cross-section through a head of a handpiece for accommodating a dental instrument produced in accordance with the present invention.

FIG. 4 is a view similar to FIG. 3, illustrating an alternative embodiment of the head of a handpiece for accommodating a dental instrument produced in accordance with the present invention.

FIG. 5 is a cross-section taken along the line V-V shown in FIG. 4.

DETAILED DESCRIPTION OF PREFERRED EMBODIMENTS

Figure 7:
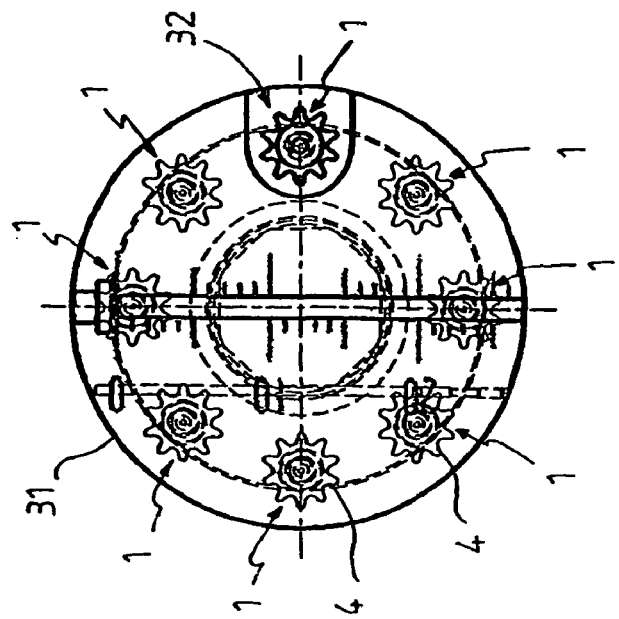
FIG. 7 is a top view of the dispenser, looking in the direction of the arrow F shown in FIG. 6.

FIGS. 1 and 2 show two types of powered, dental endodontic instruments 1. Similar to known instruments of this type, each of the instruments 1 has an active part 2 at one end and a handle 3 at another end opposite to the active part 2.

In accordance with the present invention, the handle 3 of the dental instrument 1 is provided with a rotary drive 4 which, when mounted in the head 5 of the handpiece, meshes directly with a rotary drive shaft 27 situated upstream of the head of the handpiece.

Advantageously, the rotary drive 4 of the handle 3 is a pinion having, as an example, straight cut teeth. The pinion can be produced by overmolding, or the pinion can be assembled onto the instrument or can be made unitary with the instrument.

The rotary drive 4 is capable of engaging with a drive pinion 4' associated with the drive shaft 27 which is located inside the body 6 of the handpiece in the vicinity of the head. The drive pinion 4' is mounted on the drive shaft 27 for transmitting rotational movement of the mechanical members upstream of the contra-angle into rotational movement of the instrument 1.

The profile of the pinion of the rotary drive 4 located on the handle 3, and the profile of the drive pinion 4' in the head, permit the rotary drives 4, 4' to mesh with no other operation than insertion of the instrument into the head of the contra-angle. Furthermore, the point of contact between the two pinions occurs at the bottom of the drive pinion 4', producing a right rotation of the driven shaft and in this way allowing the drive pinion 4 on the handle and the drive pinion 4' in the head to have an identical direction of rotation.

FIG. 3 shows a head 5 of a handpiece shaped for receiving the above-described dental instrument 1 so that the dental instrument 1 can be fitted to and removed from the head 5. To this end, the head 5 is provided with a bore 7, constituting the housing for the handle 3 of the instrument 1, and a retractable axial retainer 8 for retention of the handle 3 of the instrument 1 which is capable of being operated by the practitioner.

In a first embodiment, the retractable retainer 8 advantageously includes a part 8a which projects across the opening of the housing 7. The part 8a has a general horseshoe shape for engagement with a surface 13 on the handle 3 which is approximately perpendicular to the axis of the instrument 1. The projecting part 8a is integral with a ring 9 mounted concentrically on the outer periphery of the body 6 of the head. The ring 9 can be moved axially against the action of a restoring spring 10 housed between the connecting collar 11 of the handpiece and the body 6 of the head.

The projecting part 8a also includes, on its outer face, a retraction slope 12 for engagement with a combined profile formed on the end of the handle 3 of the dental instrument 1 in such a way that when the handle 3 is inserted into the head 5 of the handpiece, the combined profile of the handle 3 causes the retainer 8 to retract. The retainer 8 is returned to its rest position, responsive to the restoring spring 10, as soon as the rotary drive 4 is engaged in the head 5 and engages with the face 13 perpendicular to the instrument 1, to keep the dental instrument 1 in the head 5.

Insertion and removal of the dental power instrument 1 will be clear from the above description and will now be explained more fully below.

Fitting a dental instrument 1 to the head 5 of a handpiece is a very simple operation which simply involves presenting the head 5 over the top of the handle 3 of the instrument and pressing the head 5 down onto the handle 3 of the instrument 1 so that the resulting pressure forces the slope 12 of the retainer 8 to engage with the combined profile of the handle 3, as a result pushing the retainer 8 back against the action of the restoring spring 10. When the rotary drive 4 of the instrument 1 is fully engaged in the housing 7 of the head 5, the narrowing of the diameter of the handle 3 automatically allows the restoring spring 10 to re-extend the retainer 8, as is shown in FIG. 3. When installed in this way, the pinion 4 forming the rotary drive meshes automatically with the driving pinion 4'.

Removal of the dental instrument is equally simple. The practitioner grips the ring 9 to which the retainer 8 is connected in order to draw the retainer 8 back against the restoring spring 10, in this way releasing the opening 7 of the housing of the head 5 of the handpiece. The instrument 1 is automatically disengaged from the handpiece by gravity.

It will be appreciated that such an arrangement of the instrument 1 in the head 5 of the contra-angle makes almost all of the parts contained in the head of a conventional contra-angle unnecessary, in this way greatly reducing the cost of manufacture and offering a reduction in the size of the head of the contra-angle. This size reduction also affords better visibility when the instrument is in use.

FIGS. 4 and 5 show an alternative embodiment of the retainer 8 for engaging the instrument in the head of the handpiece. In this embodiment, the retainer 8 is a spring split ring 20 arranged on the head 5 of the handpiece in such a way that in a rest position, ends 20a and 20b of the split ring 20 project into the mouth of the opening 7 of the housing which receives the handle of the instrument. The ends 20a and 20b of the split ring 20 are retractable, by elastic deformation, responsive to the action of a pushbutton 22 located on top of the head. The pushbutton 22 bears on the split ring 20 in such a way that pressure on the pushbutton allows the handle of the instrument access to the housing.

To permit the ends 20a and 20b of the split ring 20 to automatically retract when the handle of the instrument is inserted into the housing, each end of the split ring is provided with a retraction slope 23 and 24, as is shown in FIGS. 4 and 5. The retraction slopes 23 and 24 are capable of engagement with the end of the handle 3, for pushing back the ends 20a and 20b of the split ring 20, in order to allow access to the housing 7.

As with the first embodiment, the split ring 20 is automatically repositioned as soon as the drive pinion 4 mounted on the handle 3 is fully housed inside the head 5. The ends 20a and 20b of the split ring 20 will then rest against the underside 13 of the drive pinion 4. It will be observed that each end 20a and 20b of the split ring 20 further includes a horseshoe shape, for a complete fit with the shape of a shoulder 25 formed underneath the meshing drive pinion 4. The function of the shoulder 25 will be described in more detail below.

For the alternative embodiment shown in FIGS. 4 and 5, an instrument 1 is fitted and removed in much the same way as was described in relation to the first embodiment, with the exception that the practitioner applies pressure to the pushbutton 22 to release the dental instrument 1 from the head 5 of the contra-angle.

Figure 6:
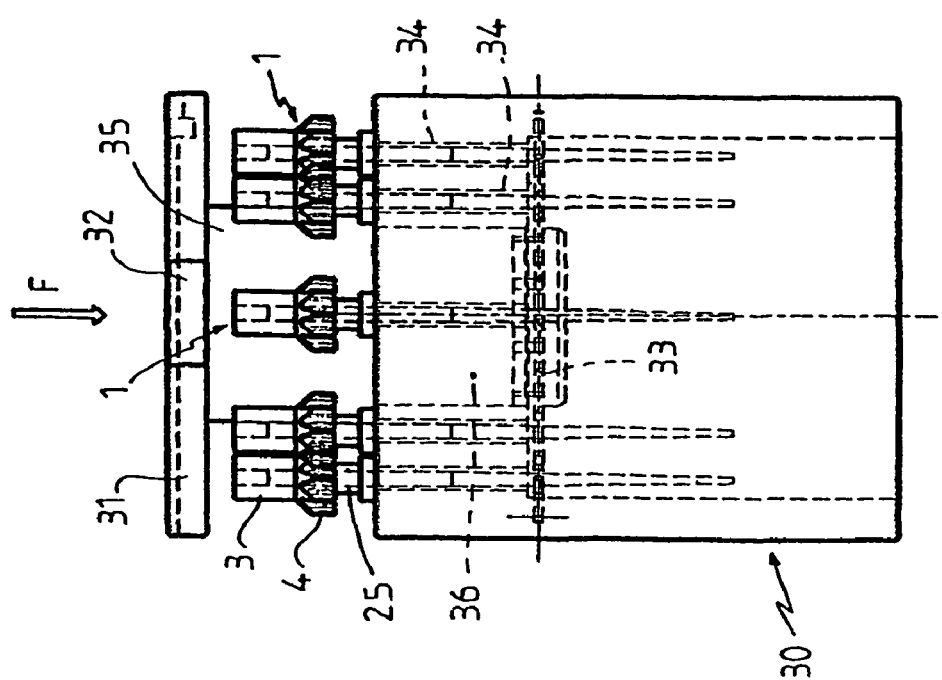
FIG. 6 is a side view of a dispenser for accommodating a plurality of dental instruments produced in accordance with the present invention.

Advantageously, each dental instrument 1 includes a shoulder 25 (or, as is shown in the alternative embodiment of FIG. 1, a shoulder 26) located in the vicinity of the meshing drive pinion 4, on the side nearest to the active part 2 of the instrument. The shoulder 25 (or 26) advantageously raises the dental instrument when positioned on a dispenser 30 (also known as a tray), as is visible in FIG. 6, in this way allowing the retainer 8 of the head 5 of the handpiece to operate without practitioner intervention. Specifically, the practitioner can load an instrument into the head simply by resting the head on top of the handle and, therefore, does not have to touch the instrument (which will have been sterilized).

The dispenser 30 includes a plurality of housings 34 for receiving the instruments 1 of the present invention, and can further advantageously include a cover 31 situated above the instruments. The cover 31 has an opening 32 for allowing the head 5 of the contra-angle to engage the handle 3 of an instrument 1.

The cover 31 can also be turned manually, by the practitioner, to position the opening 32 over an instrument 1. For this purpose, the dispenser 30 has an indexing apparatus 33 for locating the opening 32 of the cover 31 over each position for an instrument 1. To this end, and in one particular embodiment, the cover 31 forms a surface which is approximately perpendicular to the instruments 1 when arranged in the dispenser 30. This surface is in the shape of a circle, the center of which is appended to a spindle 35 that fits in a housing 36 provided in the center of the dispenser 30. The indexing apparatus 33 is located in the approximate vicinity of the free end of the spindle 35, and can take the form of a leaf spring which is capable of engagement in a slot formed at a position corresponding to one of the instruments. The leaf spring can be disengaged from the slot, by the practitioner, simply by rotating the cover.

Although the present invention has been described in connection with certain particular embodiments, the present invention further encompasses all technical equivalents of the means described.

The invention claimed is:

1. A set comprising a head for use with a handpiece of a contra-angle, and a dental instrument adapted for use with the head;
   wherein the instrument has an active part at a first end, and a handle at a second end of the instrument opposite to the first end;
   wherein the head has a body for receiving a shaft for transmitting rotational movement produced by a mechanical member associated with the handpiece, and a bore forming a housing for receiving the handle of the instrument;
   wherein the handle of the instrument includes a first rotary drive which, when mounted in the housing, is capable of meshing directly with a second rotary drive associated with the body of the head;
   wherein the first rotary drive is capable of retractable axial retention in the housing, independently of the second rotary drive;
   wherein the first rotary drive has a direction of rotation, the second rotary drive has a direction of rotation, and the direction of rotation of the first rotary drive is the same as the direction of rotation of the second rotary drive;
   wherein the first rotary drive includes a pinion capable of engaging a drive pinion located inside the body of the head, in the vicinity of the housing, and which is mounted on the shaft for transmitting the rotational movement produced by the mechanical member to the instrument, for causing rotational movement of the instrument;
   wherein the pinion of the first rotary drive has a profile, the second rotary drive includes the drive pinion located inside the body of the head, the drive pinion has a profile, and the profile of the pinion of the first rotary drive meshes with the profile of the drive pinion of the second rotary drive when the instrument is placed in the housing, and wherein the pinion of the first rotary drive and the drive pinion of the second rotary drive come into contact at bottom portions of the drive pinion of the second rotary drive;
   wherein the head is shaped to receive the instrument through an opening for insertion of the instrument into the housing so that the instrument is inserted through the opening by placing the head on the handle of the instrument; and
   wherein the head further includes a retractable retainer for engaging the handle of the instrument inserted through the opening, and wherein the retractable retainer includes a retention member which projects across the opening of the housing, and a ring coupled with the retention member and movable relative to the body of the head, against a restoring spring, wherein the ring is mounted concentrically on the body of the head.

2. The set of claim 1 wherein the instrument further includes a shoulder adjacent to the first rotary drive, on a side of the handle nearest to the active part of the instrument, for engagement by the retention member of the retractable retainer.

3. The set of claim 2 wherein the retention member further includes a sloped surface on an outer face of the retention member, and wherein the handle further includes a profile which cooperates with the sloped surface of the retention member so that when the handle is inserted into the head, the profile of the handle causes retraction of the retention member.

4. The set of claim 3 wherein the retention member further includes a horseshoe-shaped profile for cooperating with the shoulder of the instrument.

5. The set of claim 3 wherein the opening of the housing has a mouth for receiving the handle and the first rotary drive of the instrument, and wherein the sloped surface of the retention member is adjacent to the mouth of the opening.

6. The set of claim 3 wherein the sloped surface of the retention member is located along bottom portions of the housing, adjacent to the first rotary drive of the instrument.

7. The set of claim 1 wherein the opening of the housing has a mouth for receiving the handle and the first rotary drive of the instrument.

8. The set of claim 1 wherein the opening of the housing is located along bottom portions of the housing, adjacent to the first rotary drive of the instrument.

9. The set of claim 1 wherein the ring at least partially surrounds the body of the head.

10. The set of claim 1 wherein the opening is located between the bore forming the housing and exterior portions of the head, for insertion of the instrument through the opening and into the housing.

11. The set of claim 1 wherein the retractable retainer automatically engages the handle of the instrument.

12. A set comprising a head for use with a handpiece of a contra-angle, and a dental instrument coupled with the head;
   wherein the instrument has an active part at a first end, and a handle at a second end of the instrument opposite to the first end;
   wherein the head has a body for receiving a shaft for transmitting rotational movement produced by a mechanical member associated with the handpiece, and a bore forming a housing which receives the handle of the instrument;
   wherein the handle of the instrument includes a first rotary drive which, when mounted in the housing, is capable of meshing directly with a second rotary drive associated with the body of the head;
   wherein the first rotary drive is retractably axially retained in the housing, independently of the second rotary drive;
   wherein the first rotary drive has a direction of rotation, the second rotary drive has a direction of rotation, and the direction of rotation of the first rotary drive is the same as the direction of rotation of the second rotary drive;

wherein the first rotary drive includes a pinion capable of engaging a drive pinion located inside the body of the head, in the vicinity of the housing, and which is mounted on the shaft for transmitting the rotational movement produced by the mechanical member to the instrument, for causing rotational movement of the instrument;

wherein the pinion of the first rotary drive has a profile, the second rotary drive includes the drive pinion located inside the body of the head, the drive pinion has a profile, and the profile of the pinion of the first rotary drive meshes with the profile of the drive pinion of the second rotary drive when the instrument is placed in the housing, and wherein the pinion of the first rotary drive and the drive pinion of the second rotary drive come into contact at bottom portions of the drive pinion of the second rotary drive;

wherein the head is shaped to receive the instrument through an opening for insertion of the instrument into the housing so that the instrument is inserted through the opening by placing the head on the handle of the instrument; and wherein the head further includes a retractable retainer which engages the handle of the instrument inserted through the opening, and wherein the retractable retainer includes a retention member which projects across the opening of the housing, and a ring coupled with the retention member and movable relative to the body of the head, against a restoring spring, wherein the ring is mounted concentrically on the body of the head.

13. The set of claim 12 wherein the instrument further includes a shoulder adjacent to the first rotary drive, on a side of the handle nearest to the active part of the instrument, which is engaged by the retention member of the retractable retainer.

14. The set of claim 13 wherein the retention member further includes a sloped surface on an outer face of the retention member, and wherein the handle further includes a profile which cooperates with the sloped surface of the retention member so that when the handle is inserted into the head, the profile of the handle causes retraction of the retention member.

15. The set of claim 14 wherein the retention member further includes a horseshoe-shaped profile which cooperates with the shoulder of the instrument.

16. The set of claim 14 wherein the opening of the housing has a mouth which receives the handle and the first rotary drive of the instrument, and wherein the sloped surface of the retention member is adjacent to the mouth of the opening.

17. The set of claim 14 wherein the sloped surface of the retention member is located along bottom portions of the housing, adjacent to the first rotary drive of the instrument.

18. The set of claim 12 wherein the opening of the housing has a mouth which receives the handle and the first rotary drive of the instrument.

19. The set of claim 12 wherein the opening of the housing is located along bottom portions of the housing, adjacent to the first rotary drive of the instrument.

20. The set of claim 12 wherein the ring at least partially surrounds the body of the head.

21. The set of claim 12 wherein the opening is located between the bore forming the housing and exterior portions of the head, for insertion of the instrument through the opening and into the housing.

22. The set of claim 12 wherein the retractable retainer automatically engages the handle of the instrument.

* * * * *